United States Patent [19]
Shaw et al.

[11] Patent Number: 4,805,772
[45] Date of Patent: Feb. 21, 1989

[54] ADAPTORS FOR USE WITH VARIOUS CONTAINERS BEARING BAR CODE LABELING

[75] Inventors: James D. Shaw, Hilton; Michael P. Tuszynski, Rochester, both of N.Y.

[73] Assignee: Eastman Kodak Company, Rochester, N.Y.

[21] Appl. No.: 160,625

[22] Filed: Feb. 26, 1988

[51] Int. Cl.⁴ .......................................... B65D 81/30
[52] U.S. Cl. ................................. 206/443; 206/459; 211/74
[58] Field of Search ............. 206/443, 528, 446, 459; 211/74

[56] References Cited

U.S. PATENT DOCUMENTS

| 3,823,818 | 7/1974 | Shaw | 206/443 |
| 3,918,920 | 11/1975 | Barber | |
| 4,378,923 | 4/1983 | Taki | 206/443 |
| 4,434,890 | 3/1984 | Sieck et al. | 206/443 |
| 4,510,119 | 4/1985 | Hevey | 206/443 |
| 4,526,756 | 7/1985 | Wong | 206/443 |
| 4,534,465 | 8/1985 | Rothermel et al. | |
| 4,613,042 | 9/1986 | Aeschliman | 206/443 |
| 4,645,079 | 2/1987 | Hill | 206/443 |
| 4,657,132 | 4/1987 | Abdo | 206/443 |

FOREIGN PATENT DOCUMENTS

83/00393 2/1983 World Int. Prop. O. .

Primary Examiner—Joseph Man-Fu Moy
Attorney, Agent, or Firm—Dana M. Schmidt

[57] ABSTRACT

There is disclosed an adaptor constructed to allow sample containers of various sizes to fit into a tray sized for only one particular container. The adaptor includes a window that permits scanning of bar code labels on the container, locating means to restrain the adaptor from undesirable rotation in the tray, and signal means for indicating to the analyzer which size container is present.

7 Claims, 5 Drawing Sheets

4,805,772

ADAPTORS FOR USE WITH VARIOUS CONTAINERS BEARING BAR CODE LABELING

FIELD OF THE INVENTION

This invention is directed to adaptors used with tubular containers of patient sample, such as are used in clinical analyzers.

BACKGROUND OF THE INVENTION

Clinical analyzers currently in use in hospitals often do not have direct or positive sample identification associated with the container of the patient's sample. That is, an operator often is required to enter patient's data into the analyzer concerning a particular container's sample. Such an approach runs some risks, in that errors can be made in either the data entry, or the placement of the container in the predicted location of the analyzer.

To overcome this problem an improved analyzer has been provided that has positive sample identification (hereinafter, PSID). As used herein, PSID refers to the automated sampling of liquids from a container bearing machine readable patient identification, thus eliminating sources of identification error. In such an analyzer, a special container is used that has a bar code label that contains the complete identity of the patient. The bar code is read by a laser prior to the sample being aspirated into the analyzer. An example of such an approach is shown in patent application WO 83/00393.

One problem with the PSID technique is that only one or at most two specially sized containers can be used—those that fit this particular analyzer. That is, the PSID analyzer will accommodate a "conventional" tubular container, and a microcontainer that is a cup that is quite different from the "normal" tubes. The two types are distinguished based on the label that is present. However, patient samples come in tubular containers having a variety of sizes. For example, there are "standard" test tube containers that are the 16 mm sizes, some that are 13 mm in diameter, some that are 10 mm, and some that are even smaller for pediatric samples. Yet, the standard tray opening in many analyzers' trays is about 16 mm. Thus, for such analyzers, a single container having a width of about 16 mm would have to be used, and all the samples arriving in the other containers would have to be transferred somehow as such other containers would be "non-standard". Pour-off is often objectionable, since it can affect such analytes as $CO_2$, and has the potential of contamination.

Thus there has been a need, prior to this invention, to provide a PSID analyzer that will allow the direct use in that analyzer, of a variety of sizes of tubular sample containers, as supplied. Such an improved analyzer would not require the intermediate, time-consuming, and error-prone step of transfer to a special container that is the only tubular container (as opposed to a microsample container) that fits the PSID analyzer.

SUMMARY OF THE INVENTION

We have constructed adaptors that allow various sized tubes or containers to be installed "as is" in a tray having openings for a single size only, thus permitting such variety of containers to be used on a PSID analyzer.

More specifically, there is provided a tube adaptor for accommodating differently-sized containers in a tray for aspirating sample from such containers with positive sample identification, the adaptor comprising
  means for holding a container within the adaptor;
  means permitting the scanning through the adaptor, of an identification label on such a container;
  locating means for restraining the adaptor within a tray, against rotation therein;
  and means on the adaptor for generating a signal indicative of the size of the container held by the adaptor.

Thus, it is an advantageous feature of the invention that tubular containers of various sizes can be sampled on a PSID analyzer constructed to receive only a standard, single-sized container.

It is a related advantageous feature of the invention that such differently-sized tubular containers can be used on such an analyzer without transfer to another container.

It is another advantageous feature of the invention that the same basic design is available to the adaptor of this invention, for three differently-sized tubular containers, thus minimizing the mold changes that are needed.

Other advantageous features will become apparent upon reference to the following Description of the Preferred Embodiments, when read in light of the attached drawings.

DESCRIPTION OF THE PREFERRED EMBODIMENTS

The invention is described herein in connection with preferred embodiments, in which the non-standard tubular containers that are accommodated are a pediatric capillary tube, a 13 mm (nominal width) tube, and a 10 mm (nominal width) tube. In addition, the invention is useful to accommodate tubular containers that have any width, the adaptor being adjusted internally to accommodate that width, as is explained hereinafter. Furthermore, although the invention is described for its preferred use in a PSID analyzer, it is also useful in any device requiring the scanning of labels on containers that come in a variety of sizes.

Descriptives such as "up", "down", "vertical" and the like refer to orientations of parts in their normal usage in the invention.

Figure 1:
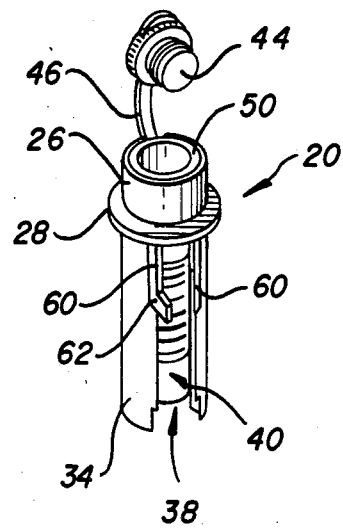
FIG. 1 is an isometric view of an adaptor constructed in accordance with the invention.

Referring now to FIG. 1, an adaptor 20 constructed in accord with the invention is useful in holding a pediatric capillary container or tube 40. Such a tube holds about 1 ml of liquid, and comprises a body 42, a cap 44, and a strap 46 joined to the cap and wrapped around at 48 to the head 50 of the body 42, FIG. 2.

Figure 5:
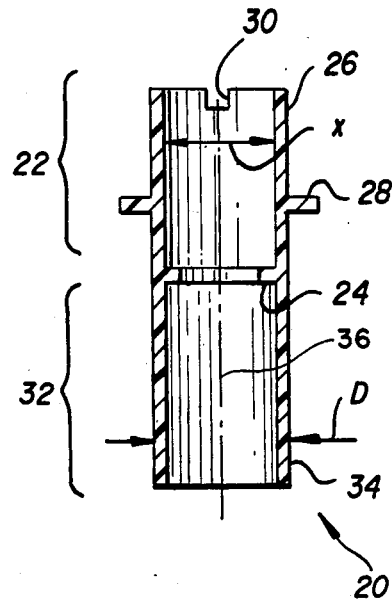
FIG. 5 is a section view taken generally along the line V—V of FIG. 4.

Adaptor 20 comprises an upper portion 22, a lower portion 32, and an interior shoulder 24 separating the two portions, FIG. 5. Shoulder 24 helps provide proper centering of container 40 within the adaptor. Upper portion 22 features a vertical sidewall 26, an exterior support lip 28, and a notch 30 in a sidewall 26 to receive strap 46 of the container, FIG. 2. The outside diameter of portion 22 is chosen to be compatible with a pierceable evaporation cap 47. Notch 30 permits sufficient extension of portion 22 above strap 46 to engage evaporation cap 47 with the strap still in place. The cap is preferred to reduce evaporation of very small sample volumes. Lower portion 32 comprises a skirt sidewall 34, that is wrapped around an axis of symmetry 36, FIGS. 3, 5, and 8, that leaves the front of sidewall 34 open and exposed for reading the container inside. Most preferably, the wrap-around of sidewall 34 is such as to form an angle alpha that is at least from about 50 degrees to about 90 degrees, FIG. 8. That is, the sidewall is wrapped around axis 36 for no more than about 270 degrees to about 310 degrees, creating window 38 for permitting bar code scanning of a label on container 40. Sidewall 34 extends above interior shoulder 24 to exterior lip 28, FIG. 5.

Figure 2:
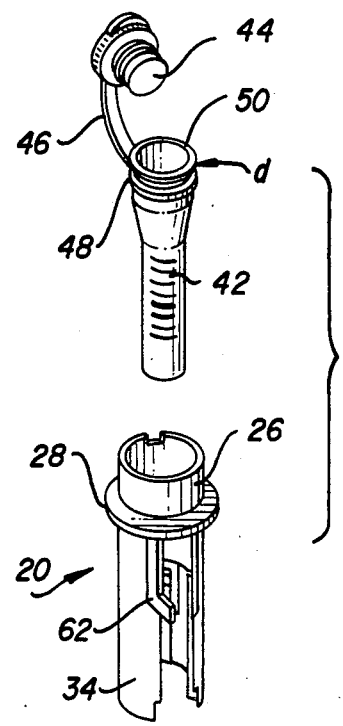
FIG. 2 is an exploded isometric view similar to that of FIG. 1, illustrating the fit of a pediatric capillary tube in the adaptor.

The interior diameter "x" of sidewall 26, FIG. 5, is selected to provide a snug fit with the exterior diameter "d", FIG. 2, of head 50 of container 40.

Lower portion 32 has several further features as well. Sidewall 34 includes flanges 60 at each side of window 38, FIGS. 1, 3 and 8, that kept the adaptor from rotating in a tray. In addition, one of flanges 60 includes means for generating a signal that is indicative of the size of the container held by the adaptor. Preferably those means include a mechanical flag 62 that projects out beyond its flange 60, to trigger a sensor (not shown) on the analyzer. The flag is distinctive based upon its vertical position, or height "h", FIG. 3, below lip 28. The type of signal generating means that is used is not critical. Other types, besides mechanical fingers, include magnetic, and optically reflective surfaces that coact with appropriate means on the analyzer.

The exterior diameter "D", FIG. 5, of sidewall 34, is adjusted to fit inside the standard opening of a tray, as noted hereinafter.

Figure 7A:
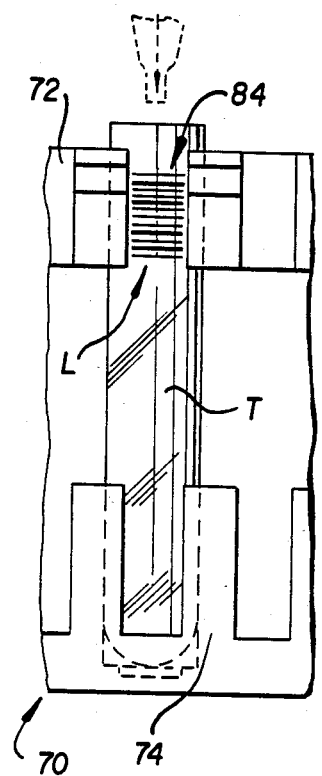
FIG. 7A is a fragmentary front elevational view of the tray of FIG. 6, illustrating it holding a conventional tube for PSID reading and then sampling, in a PSID analyzer.
Figure 7B:
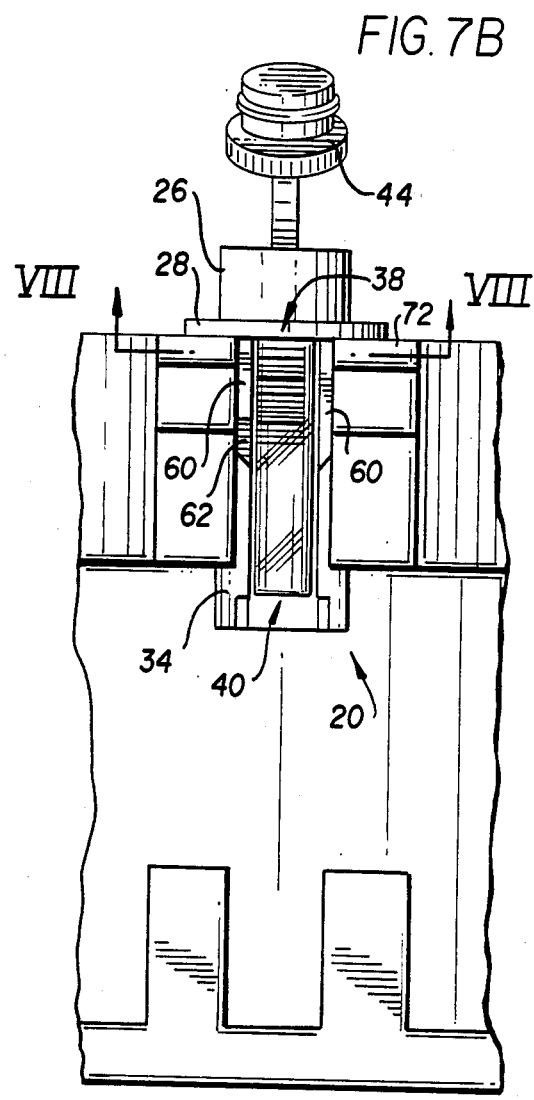
FIG. 7B is a view generally identical to that of FIG. 7A, except with the tube adaptor of FIG. 1 in place in the tray.
Figure 8:
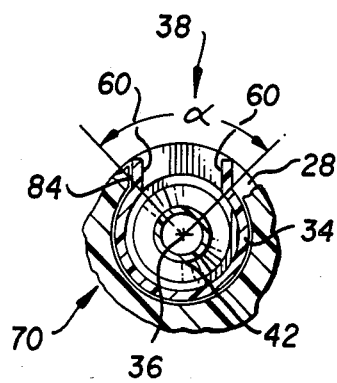
FIG. 8 is a section view taken generally along the line VIII—VIII of FIG. 7B.
Figure 6:
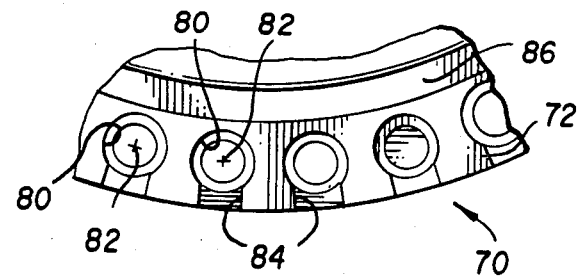
FIG. 6 is a fragmentary plan view of a container tray with which the adaptors of the invention are used.

Turning next to FIGS. 6–8, tray 70 is a conventional container tray for an analyzer, constructed to hold a plurality of sample containers around its periphery. Preferably it is mounted for rotation, and thus is generally cylindrical, or segmented cylindrical, in shape. It rotates to carry the sample containers preferably past a read station, not shown, and an aspirating station (also not shown). Thus, it comprises an outer, upper support lip 72 and lower support lip 74, FIG. 7A, that is molded with generally circular openings 80, FIG. 6, that extend around an axis 82, except for a read window 84, FIGS. 6 and 7A. The interior diameter of opening 80 is that designed to hold a standard, labeled tube "T", FIG. 7A, for use in a PSID analyzer, for example a tube that has a nominal outside diameter of 16 mm. Such a tray first permits a label "L", FIG. 7A, to be read, and then a metering tip, shown in phantom, to be inserted into the tube to aspirate out sample.

Adaptor 20 fits into openings 80 to hold container 40 as shown in FIG. 7B. Exterior lip 28 of the adaptor sits on lip 72 of the tray, with sidewall 34 extending down through opening 80. As shown more clearly in FIG. 8, flanges 60 keep the adaptor from rotating within the tray, so that read window 38 of the adaptor is aligned with read window 84 of the tray.

Preferably tray 70 has a groove 86 in upper lip 72, FIG. 6, which groove gives space for removed cap 44 and strap 46.

Still other sized tubular containers are commonly used, and the adaptors for these are illustrated in the remaining Figures. Parts similar to those previously described bear the same reference numeral, to which the distinguishing suffixes "a" of "b", respectively, are added for each alternative embodiment.

For example, the adaptor 20a, FIG. 9, for a nominal width 13 mm container $T_1$, FIG. 11, comprises upper portion 22a, lower portion 32a, support lip 28a, and interior shoulder 24a, constructed generally as before except as noted hereinafter. In this case shoulder 24a is the upper stop that limits the upper movement of a container $T_1$ in the adaptor, FIG. 11.

Figure 10:
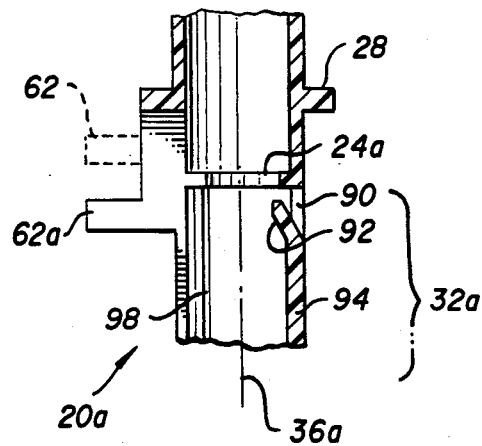
FIG. 10 is a section view taken generally along the line X—X of FIG. 9.
Figure 9:
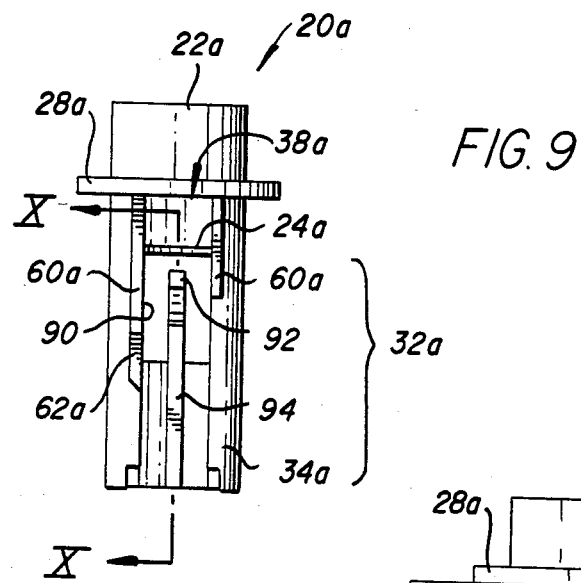
FIG. 9 is a front elevational view similar to that of FIG. 3, except of an alternative embodiment and without the tubular sample container.

Unlike adaptor 20, adaptor 20a includes several additional features in the back of sidewall 34a, FIGS. 9 and 10. Thus, an opening 90 is provided, and a spring finger 92 is molded to extend up into the opening. Preferably, FIG. 10, finger 92 is shaped to also extend towards axis 36a, to provide a bias against tube $T_1$. Such extension of finger 92 is shaped to accommodate whatever sized tubular container is desired for that adaptor. Most preferably, finger 92 is an extension of a vertical support rib 94 that also extends out towards axis 36a. Rib 94 and finger 92 function to frictionally engage container $T_1$ within lower portion 32a of adaptor 20a, FIG. 11. Optionally, additional vertical support ribs 98 (FIG. 10) can be molded on the inside surface of sidewall 34a, for centering and holding container $T_1$.

As is apparent from FIG. 10, flag 62a is located at a different height than was flag 62 (in phantom lines), so as to designate that it is an adaptor for tubular container $T_1$.

Figure 11:
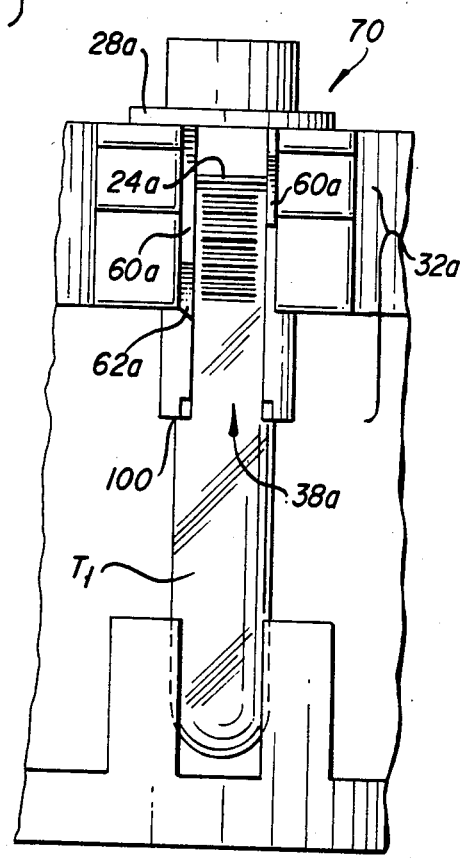
FIG. 11 is an elevational view similar to that of FIG. 7B, but illustrating the adaptor of FIG. 9 with its tubular container.

FIG. 11 illustrates the use of adaptor 20a to hold container $T_1$ suspended in tray 70. As before, window 38a, FIG. 9, of the adaptor allows bar code scanning of the container, and flanges 60a keep the adaptor from rotating within the tray. Thus, the same tray 72 is used to hold adaptors 20a as is used for adaptors 20.

Figure 12:
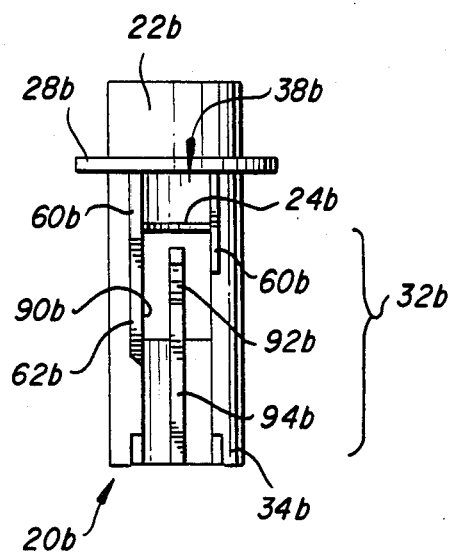
FIG. 12 is an elevational view similar to that of FIG. 9, but illustrating yet another alternative embodiment.
Figure 13:
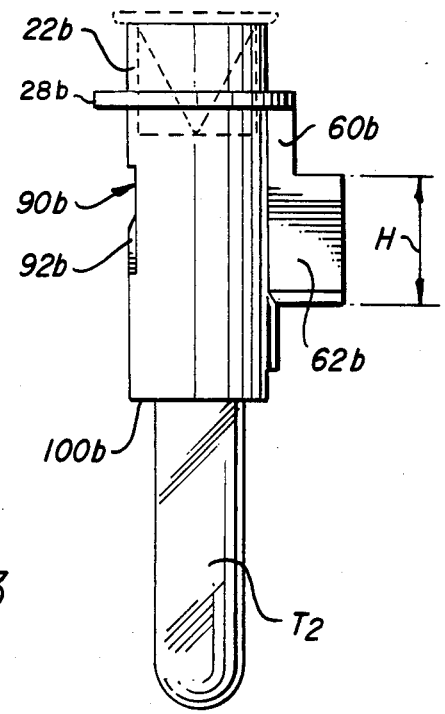
FIG. 13 is a side elevational view of the adaptor of FIG. 12, showing its use with a tubular container.

Adaptor 20b, FIGS. 12 and 13, is used to hold a container $T_2$ of yet another nominal width, for example 10 mm. It is similar to adaptor 20a, so that similar parts bear the same reference numeral with the "b" suffix. Thus, it has upper portion 22b, interior shoulder 24b, exterior lip 28b, lower portion 32b, sidewall 34b, read window 38b (with the same exposure angle alpha as for adaptor 20), flanges 60b, rear opening 90b, bias finger 92b, and rib 94b. Bias finger 92b is constructed to allow either container $T_1$ or $T_2$ to be used, to facilitate the molding of adaptors 20a and 20b. However, the distinguishing aspect of adaptor 20b is its flag 62b. As shown more particularly in FIG. 13, flag 62b extends for a greater height H, than either flanges 62 or 62a, and thus designates adaptor 20b as being for container $T_2$.

Adaptor 20b fits (not shown) into the same tray 70 as described above, with its tube $T_2$, FIG. 13, which however does not extend down as far towards lower lip 74 of the tray (shown in FIG. 7A).

An additional feature optionally present in both adaptors 20a and 20b, is that the length of sidewall 34a and 34b, down to bottom edge 100 or 100b, FIGS. 11 and 13, is useful in sighting whether or not there is sufficient fluid present in the container ($T_1$ or $T_2$). If the fluid level is below edge 100 or edge 100b, then the fluid can be transferred to a microsample container that sits in the top of upper portion 22b shown in phantom, FIG. 13, for more ready access by the analyzer.

The invention has been described in detail with particular reference to preferred embodiments thereof, but it will be understood that variations and modifications can be effected within the spirit and scope of the invention.

What is claimed is:

1. A tube adaptor for accommodating differently-sized containers in a tray for aspirating sample from such containers with positive sample identification, the adaptor comprising
    means for holding a container within the adaptor;
    means permitting the scanning through the adaptor, of an identification label on such a container;
    locating means for restraining said adaptor within a tray, against rotation therein;
    and means on said adaptor for generating a signal indicative of the size of the container held by the adaptor.

2. An adaptor as defined in claim 1, and further including means for frictionally engaging a container to prevent it from rotating within the adaptor.

3. A tube adaptor as defined in claim 1, and further including means in the adaptor for mounting a cup above such a container for holding a small fraction of the liquid contents of such a container.

4. A tube adaptor as defined in claim 1, and further including stop means for positively locating such a container with its top edge at a predetermined location spaced along the axis of the adaptor.

5. A tube adaptor for accommodating differently-sized containers in a tray for aspirating sample from such containers with positive sample identification, the adaptor comprising
    an upper portion and a lower portion, said portions being divided by a shoulder and centered on an axis of symmetry,
    said upper portion comprising an open container for holding an auxiliary cup,
    said lower portion comprising a sidewall for enclosing a container abutted up against said dividing shoulder, said sidewall being wrapped around said axis of symmetry for no more than from about 270 degrees to about 310 degrees to leave open a gap permitting bar code scanning of a container,
    means for restraining said adaptor and an enclosed container against rotation within a tray;
    and means on said lower portion for generating a signal indicative of the size of a container held by the adaptor.

6. A tube adaptor as defined in claim 5, and further including means for frictionally engaging such differently-sized container to prevent it from rotating within said adaptor.

7. A tube adaptor as defined in claim 1 or 5, wherein the overall length of said adaptor is selected to be predictable of an adequate level of liquid present in a container mounted in the adaptor.

* * * * *

UNITED STATES PATENT AND TRADEMARK OFFICE
CERTIFICATE OF CORRECTION

PATENT NO.   : 4,805,772

DATED        : February 21, 1989

INVENTOR(S)  : Shaw, James D. and Tuszynski, Michael P.

Figure 3:
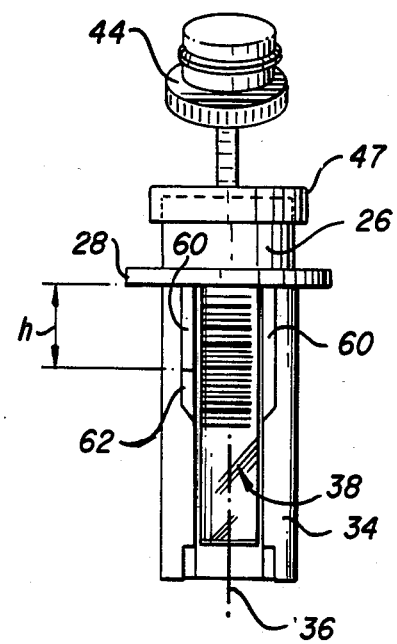
FIG. 3 is a front elevational view of the adaptor ad the tube of FIG. 1.
Figure 4:
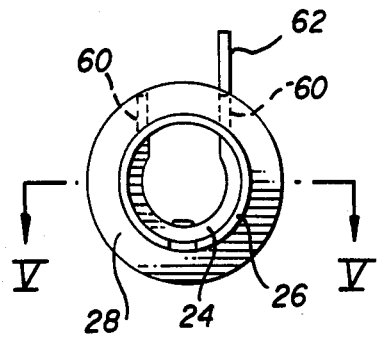
FIG. 4 is a plan view of the adaptor of FIG. 1 by itself.

It is certified that error appears in the above-identified patent and that said Letters Patent is hereby corrected as shown below:

Col. 2, line 37 should read:
  --FIG. 3 is a front elevational view of the adaptor and--
Col. 4, line 33 should read:
  --the distinguishing suffixes "a" or "b", respectively, are--

Signed and Sealed this

Fourteenth Day of November, 1989

*Attest:*

JEFFREY M. SAMUELS

*Attesting Officer*   *Acting Commissioner of Patents and Trademarks*